United States Patent [19]
Ho et al.

[11] Patent Number: 4,835,188
[45] Date of Patent: * May 30, 1989

[54] SPRAY DRIED IBUPROFEN

[75] Inventors: Ying T. R. Ho, Haddonfield; Robert G. Blank, Vineland, both of N.J.

[73] Assignee: American Home Products Corporation (Del.), New York, N.Y.

[*] Notice: The portion of the term of this patent subsequent to Jan. 27, 1998 has been disclaimed.

[21] Appl. No.: 130,718

[22] Filed: Dec. 8, 1987

[51] Int. Cl.$^4$ .............................................. A61K 31/74
[52] U.S. Cl. .................................. 514/570; 424/499; 514/974
[58] Field of Search ................ 514/974, 570; 424/499

[56] References Cited

U.S. PATENT DOCUMENTS

| | | | |
|---|---|---|---|
| 4,569,937 | 2/1986 | Baker et al. | 514/282 |
| 4,681,897 | 6/1987 | Brand | 514/557 |
| 4,695,591 | 9/1987 | Hanno | 514/781 |
| 4,726,966 | 2/1988 | Kawashima et al. | 514/974 |

FOREIGN PATENT DOCUMENTS 0190826  8/1986  European Pat. Off. ............ 514/974

Primary Examiner—Joseph L. Schofer
Assistant Examiner—Peter F. Kulkosky
Attorney, Agent, or Firm—John W. Routh

[57] ABSTRACT

A therapeutic taste-neutral powder form of ibuprofen obtained by spray-drying a dispersion of ibuprofen and ethyl cellulose in water having a plasticizer dissolved or suspended therein.

6 Claims, No Drawings

SPRAY DRIED IBUPROFEN

BACKGROUND OF THE INVENTION (a) Field of the Invention

This invention relates to a novel therapeutic form of spray dried ibuprofen having a neutral taste which can be formulated into, for example, chewable tablets and fast dissolving dosage forms as described in U.S. Pat. Nos. 4,305,502 and 4,371,516. More specifically this invention relates to a taste neutral spray dried powder formed by spray drying a dispersion of ibuprofen and ethylcellulose in water having a plasticizer dissolved or suspended therein. By taste-neutral it is meant that the powder has essentially no taste and is not sweet nor bitter.

(b) Prior Art

Ibuprofen, a widely used analgesic and antipyretic, is not palatable enough to be used in chew-type tablets for those people who do not swallow whole solidtype dosage forms.

The use of flavor agents eg. chocolate, banana, orange, lemon, licorice, root beer, and raspberry, in particular, have been proposed for bitter tasting drugs. These agents are not dependable masking ingredients. Mint flavors can be useful in ameliorating a chalky taste parameter. Bitter properties, however, are very difficult to mask to any great extent, particularly, when they do not mimic the expected natural taste of the flavor agent.

Other properties including mouthfeel also need to be addressed in consideration of the oral acceptance of chewable or chew-type tablets.

The fast dissolving dosage forms described in U.S. Pat. Nos. 4,305,502 and 4,371,516 are manufactured to disintegrate in water within five seconds or less and hence dissolve rapidly in the saliva of the mouth. Heretofore the use of such dosage forms was restricted to pharmaceuticals which had a neutral taste or a slightly disagreeable taste which could be masked by a flavoring agent. Pharmaceuticals with a bitter taste such as acetaminophen and ibuprofen, however, could not heretofore be used in such dosage forms.

SUMMARY OF THE INVENTION

According to this invention, a novel therapeutic taste-neutral powder form of spray-dried ibuprofen is provided which can be formulated into chewable tablets and the like. The powder is formed by spray drying a dispersion of ibuprofen and ethyl cellulose in water having a plasticizer dissolved or suspended therein. Preferably a small amount of a suspending agent to suspend the ibuprofen in the dispersion is employed.

According to another aspect of this invention, a pharmaceutical dosage form for oral administration as a solid is provided, which dosage form can be disintegrated by water at 37° C. within ten seconds, and comprises as the pharmaceutical agent incorporated therein the taste neutral powder form of spray dried ibuprofen of this invention.

DETAILS OF THE INVENTION

The ibuprofen useful in this invention is the pharmaceutical grade in finely powdered or micronized form. The ethyl cellulose useful in this invention is also National Formulary or pharmaceutical grade. Suitable grades are the AQUACOAT brand marketed by FMC Corporation of Newark, Del. and the SURELEASE brand marketed by Colorcon Incorporated, West Point, Pa.

The plasticizers useful in this invention include dibutyl sebacate, glycerin, propylene glycol, triacetin, triethyl citrate, and low molecular weight polyethylene glycols such as CARBOWAX 600, marketed by Union Carbide Corp. of Danbury, Conn. A suitable plasticizer is UNIFLEX brand of dibutyl sebacate marketed by Union Camp Corp. of Jacksonville, Fla.

The suspending agents to suspend the ibuprofen in the dispersion prior to spray drying can be of usual type such as microcrystalline cellulose, polyvinylpyrrolidone, and the like. The weight percent of ibuprofen in the taste neutral powder can be from about 63% to 77% by weight and the weight percent of the ethylcellulose can range from about 25% to 40%, preferably about 28% to 40% by weight. At about 25% by weight of ethylcellulose, there is no bitter taste and the powder is taste neutral. The weight percent of plasticizer in the taste neutral powder can be from about 2% to 7% by weight.

Spray dryers can be of the usual laboratory or commercial type. Suitable spray dryers are manufactured by Buchi Laboratoriums-Technik AG, by the Anhydro Company of Attleboro, Mass. and by Niro Atomizer Inc., of Columbia, Md. The spray dryer employed in the following examples was a Niro Portable Spray Dryer, Model No. 21231-0001. The operating conditions include a variable air inlet temperature, a variable outlet temperature, a variable air pressure of compressed air driving the atomizer wheel, and a variable feed rate.

The following examples illustrate the formation of the taste-neutral spray dried ibuprofen powder of the invention. In these examples, the ibuprofen was obtained from Ethyl Corporation, Baton, Rouge, La., and the ethyl cellulose was obtained from FMC Corporation, Newark, Del. as AQUACOAT. It was a 30% solids dispersion in water of the standard type having an ethoxy content of 48.0% to 49.5%.

EXAMPLE I

In this example, the feed mixture to the spray dryer was composed of the following materials.

| Ingredient | Weight % Solids in powder | Grams Ingredient in suspension | Grams Solids in suspension |
|---|---|---|---|
| Ibuprofen, USP | 74 | 200 | 200 |
| Polyvinylpyrrolidone |  | 0.4 | 0.4 |
| AQUACOAT brand of Ethyl Cellulose, NF | 22 | 200 | 60 |
| Uniflex brand of Dibutyl Sebacate | 4 | 12 | 12 |
| Deionized Water | — | 1100 |  |
| Total: | 100% | 1512.4 grams | 272.4 |

Approximately 200 grams of finely divided ibuprofen were passed through a 20 mesh (Tyler) screen and 200 grams of the screened ibuprofen were retained. The 1200 grams of deionized water were placed in a stainless steel mixing vessel equipped with a Lightnin mixer. With mixing and slowly added to the water were the polyvinylpyrrolidone and the ibuprofen powder. Mixing was continued for 30 minutes. In a separate stainless steel mixing vessel equipped with a Lightnin mixer the dibutyl sebacate was mixed with the AQUACOAT brand of ethyl cellulose for 30 minutes. The ethyl cellulose-dibutyl sebacate mixture was then added to the ibuprofen suspension and mixed for 30 minutes. The dispersion was then transferred to the feed hopper of the Niro Portable Spray Dryer.

The spray dryer was operated such that an air outlet temperature of approximately 37°–39° C. and a spray rate of 32–35 ml/minute were maintained throughout the run.

The spray dried powder with the 22% ethyl cellulose coat had a slightly bitter taste. The moisture content of the powder was 0.36–0.50%.

EXAMPLE II

In this example, the feed mixture to the spray dryer was composed of the following materials.

| Ingredient | Weight % Solids in powder | Grams Ingredient in suspension | Grams Solids in suspension |
|---|---|---|---|
| Ibuprofen, USP | 70.92 | 100 | 100 |
| AQUACOAT brand of Ethyl Cellulose, NF | 21.28 | 100 | 30 |
| Uniflex brand of Dibutyl Sebacate | 4.26 | 6 | 6 |
| Microcrystalline Cellulose | 3.54 | 5 | 5 |
| Deionized Water | — | 494 | |
| Total: | 100% | 705 grams | 141 |

To the 100 grams of AQUACOAT brand of ethyl cellulose as a 30% solids dispersion in water contained in a mixing vessel equipped with a Lightnin mixer were added the 6 grams of dibutyl sebacate and the dispersion was mixed for 30 minutes. The 100 grams of ibuprofen prescreened through 20 mesh (Tyler) were added to 494 grams of deionized water contained in a separate mixing vessel equipped with a Lightnin mixer to which the microcrystalline cellulose had previously been added. The ethyl cellulose-dibutyl sebacate dispersion was then mixed with the ibuprofen suspension for 30 minutes. The microcrystalline cellulose was added to the ibuprofen suspension to aid in maintaining the ibuprofen in suspension so that it does not settle out in the spray drier feed hopper. The dispersion was then transferred to the feed hopper of the Niro Portable Spray Dryer. The operating conditions for the spray drier were the same as in Example 1.

The spray dried powder had a slightly bitter taste indicating that more ethyl cellulose was required to achieve a taste neutral product.

EXAMPLE III

In this example, the feed mixture to the spray dryer was composed of the following materials.

| Ingredient | Weight % Solids in powder | Grams Ingredient suspension | Grams Solids in suspension |
|---|---|---|---|
| Ibuprofen, USP | 66.38 | 100.0 | 100.0 |
| AQUACOAT brand of Ethyl Cellulose, NF | 26.54 | 133.3 | 40.0 |
| Citroflex-2 brand of triethyl citrate | 5.31 | 8.0 | 8.0 |
| Microcrystalline Cellulose | 1.66 | 2.5 | 2.5 |
| Polyvinylpyrrolidone | 0.15 | 0.225 | 0.225 |
| Deionized Water | — | 760.8 | |
| Total: | 100.02 | 1004.825 | 150.725 |

To the 133.3 grams of AQUACOAT brand of ethyl cellulose as a 30% solids dispersion in water contained in a mixing vessel equipped with a Lightnin mixer were added the 8 grams of Citroflex-2 and the dispersion was mixed for 30 minutes. The 100 grams of ibuprofen prescreened through 20 mesh (Tyler) were added to the 760.8 grams of water to which the microcrystalline cellulose and polyvinylpyrrolidone had previously been added and mixed. The ethyl cellulose dispersion was added to the ibuprofen suspension and mixed for 30 minutes until a homogeneous suspension is formed. The dispersion was then transferred to the feed hopper of the Niro Portable Spray Dryer.

The spray dryer was operated such that the air inlet temperature was about 80° C. and an air outlet temperature of 37°–39° C. was maintained during the run. The feed rate to the spray nozzle was about 32–35 ml/minute.

The spray dried powder had a moisture content of 0.5% and was taste neutral. After several seconds it produced a slightly bitter sensation at the back of the mouth indicating that slightly more ethyl cellulose was required to achieve a completely satisfactory product.

EXAMPLE IV

This example describes the preparation of fast dissolving dosage forms using the spray dried taste-neutral ibuprofen of Example 3 and other ingredients as follows:

| Ingredients | Weight % suspension | Grams Ingredient per 500 grams suspension |
|---|---|---|
| Gelatin, BY 19/50 | 4.00 | 20.00 |
| Mannitol, granular | 3.00 | 15.00 |
| Deionized water | 67.50 | 337.50 |
| NUTRASWEET, NF | 0.60 | 3.00 |
| Anise/Juicy Fruit #669 | 0.75 | 3.75 |
| Red FD&C #40 (1% Solution) | 0.25 | 1.25 |
| Sodium lauryl sulfate | 1.00 | 5.00 |
| Sweetness Flavor #284 | 0.10 | 0.50 |
| Powder, Example 3 | 22.80 | 114.00 |
| Total: | 100.00 | 500.00 |

The procedure for preparing a batch of the above suspension takes place in two stages, i.e. the preparation of the gelatin base and the addition of the pharmaceutical agent.

The gelatin base is prepared by adding the gelatin to the deionized water at 30° C. and mixing until the gelatin is dissolved. The solution is then cooled to 25° C. and the mannitol, the sodium lauryl sulfate, the sweetener, and the flavors are separately added and dissolved.

The freeze dryer employed in this example was a Virtis 25 SRC Model Freeze Dryer. The fast dissolving dosage forms are prepared by dosing 500 milligrams of the suspension of ibuprofen into each well in a thermoformed blister tray containing 10 wells per tray. The filled trays are placed in a larger tray containing a dry ice-methanol mixture. When the suspensions in the wells are frozen, the samples are placed on the freeze dryer trays at a shelf temperature of −45° C.

When the samples have reached a temperature of −45° C., as determined by a probe in a well, the condenser is turned on and the freezer turned off. The condenser temperature is brought to between −40° and −45° C. and the vacuum is turned on to between 50 and 60 millitorrs. The heater is then turned on and the shelf temperature is adjusted to 50°–55° C. The heat-dry cycle lasts for 4 hours. The vacuum, the condenser and the heater are turned off and the samples removed. The wafers from each batch are removed from the wells in the trays. They are white in color and each weights about 165 milligrams of which about 80 milligrams is ibuprofen. The wafers from each batch when placed on the tongue exhibit a fruit flavor with a very slight bitter after taste. When placed in water at 37° C. the wafers disintegrate in less than ten seconds.

EXAMPLE V

This example describes the preparation of a chewable tablet using the spray dried taste neutral ibuprofen of Example 3 and other ingredients as follows:

| Ingredients | Weight |
| --- | --- |
| Powder of Example 3, 70% | 120.50 mg |
| Mannitol powder, USP | 120.50 mg |
| Confectionous sugar, 6X, RF | 60.25 mg |
| Magnesium stearate | 2.00 mg |
| Sorbitol q.s. to | 500.00 mg |
| Total | 500.00 mg |

The powder of Example 3 contains 66.4% by weight or 80 mg of ibuprofen. The ingredients are mixed in a suitable mixer and formed into tablets. The tablets when chewed in the mouth have a neutral taste and good mouthfeel. The taste could be improved by incorporation into the tablet of suitable flavoring agents such as a mint flavoring agent.

We claim:

1. A therapeutic taste neutral powder form of spray-dried ibuprofen which consists essentially of, based upon the weight of the powder, about 63% to 77% by weight ibuprofen, about 25% to 40% by weight ethyl cellulose and about 2% to 7% by weight of a plasticizer, the powder having been spray dried from a dispersion of the ibuprofen and ethyl cellulose in water having a plasticizer dissolved or suspended therein.

2. In a pharmaceutical dosage form for oral administration as a solid, which dosage form can be disintegrated by water within ten seconds, the improvement which comprises incorporating into such dosage form as the pharmaceutical substance a therapeutic taste-neutral powder form of spraydried ibuprofen which consists essentially of, based upon the weight of the powder, about 63% to 77% by weight ibuprofen, about 25% to 40% by weight ethyl cellulose and about 2% to 7% by weight of a plasticizer, the powder having been spray dried from a dispersion of the ibuprofen and ethyl cellulose in water having a plasticizer dissolved or suspended therein.

3. In a pharmaceutical dosage form for oral administration as a solid chewable taste-neutral tablet containing ibuprofen, the improvement which comprises incorporating into such tablet as the pharmaceutical substance a therapeutic taste-neutral powder form of spraydried ibuprofen which consists essentially of, based upon the weight of the powder, about 63% to 77% by weight ibuprofen, about 25% to 40% by weight ethyl cellulose and about 2% to 7% by weight of a plasticizer, the powder having been spray dried from a dispersion of the ibuprofen and ethyl cellulose in water having a plasticizer dissolved or suspended therein.

4. The taste neutral powder of claim 1 wherein the ethyl cellulose is about 28% to 40% by weight and the plasticizer is dibutyl sebacate.

5. The dosage form of claim 2 wherein the ethyl cellulose is about 28% to 40% by weight and the plasticizer is dibutyl sebacate.

6. The dosage form of claim 3 wherein the ethyl cellulose is about 28% to 40% by weight and the plasticizer is dibutyl sebacate.

* * * * *

UNITED STATES PATENT AND TRADEMARK OFFICE
CERTIFICATE OF CORRECTION

PATENT NO. : 4,835,188

DATED : May 30, 1989

INVENTOR(S) : Ho, Ying T.R.

It is certified that error appears in the above-identified patent and that said Letters Patent is hereby corrected as shown below:

Title page:

Delete the following-- [*] Notice: The portion of the term of this patent subsequent to Jan. 27, 1998 has been disclaimed.--.

Signed and Sealed this

Fifteenth Day of May, 1990

*Attest:*

HARRY F. MANBECK, JR.

*Attesting Officer*      *Commissioner of Patents and Trademarks*